United States Patent [19]

Cheney

[11] Patent Number: 4,827,496
[45] Date of Patent: May 2, 1989

[54] LEG AND ANKLE HOLDER FOR ASSISTING MEDICAL AND RADIOLOGICAL PROFESSIONALS IN X-RAY EXAMINATION AND FILMING OF THE ANKLE AND FOOT STRUCTURE

[75] Inventor: Prescott J. Cheney, Concord, Mass.

[73] Assignee: M. C. Johnson Co., Inc., Leominster, Mass.

[21] Appl. No.: 75,537

[22] Filed: Jul. 20, 1987

Related U.S. Application Data

[63] Continuation-in-part of Ser. No. 877,127, Jun. 23, 1986, abandoned.

[51] Int. Cl.⁴ .............................................. A61B 6/00
[52] U.S. Cl. .................................... 378/180; 378/208; 269/328
[58] Field of Search ............... 378/177, 180, 207, 204, 378/205, 208, 209; 128/90; 269/328

[56] References Cited

U.S. PATENT DOCUMENTS

| 3,521,876 | 7/1970 | Smith | 378/208 |
| 4,232,681 | 11/1980 | Tulaszewski | 378/208 |
| 4,299,210 | 11/1981 | Santy | 128/90 |
| 4,323,080 | 4/1982 | Melhart | 378/208 |
| 4,407,277 | 10/1983 | Ellison | 269/328 |
| 4,443,005 | 4/1984 | Sugarman et al. | 269/328 |
| 4,615,516 | 10/1986 | Stulberg et al. | 269/328 |

FOREIGN PATENT DOCUMENTS 2920394 11/1980 Fed. Rep. of Germany ...... 269/328

Primary Examiner—Carolyn E. Fields
Assistant Examiner—Joseph A. Hynds
Attorney, Agent, or Firm—Charles R. Fay

[57] ABSTRACT

A foot and ankle positioning and holding fixture for medical examination and X-ray of the foot and ankle, with film holding means enabling views in a single film of both side and top for easier comparison. The fixture is easily adjustable for dorsiflexion and internal and external rotation.

11 Claims, 3 Drawing Sheets

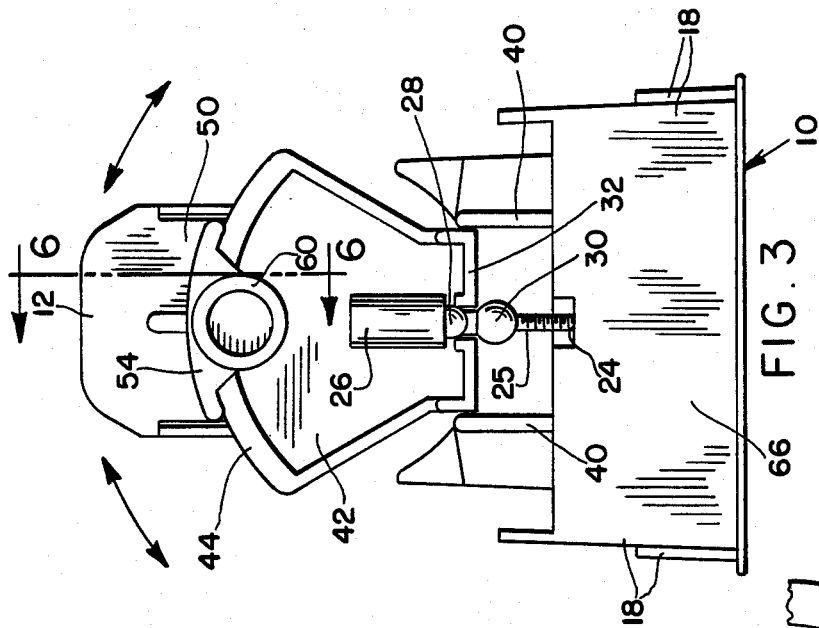
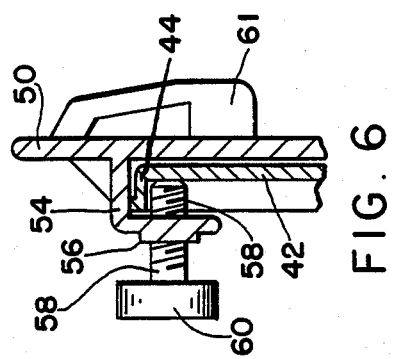
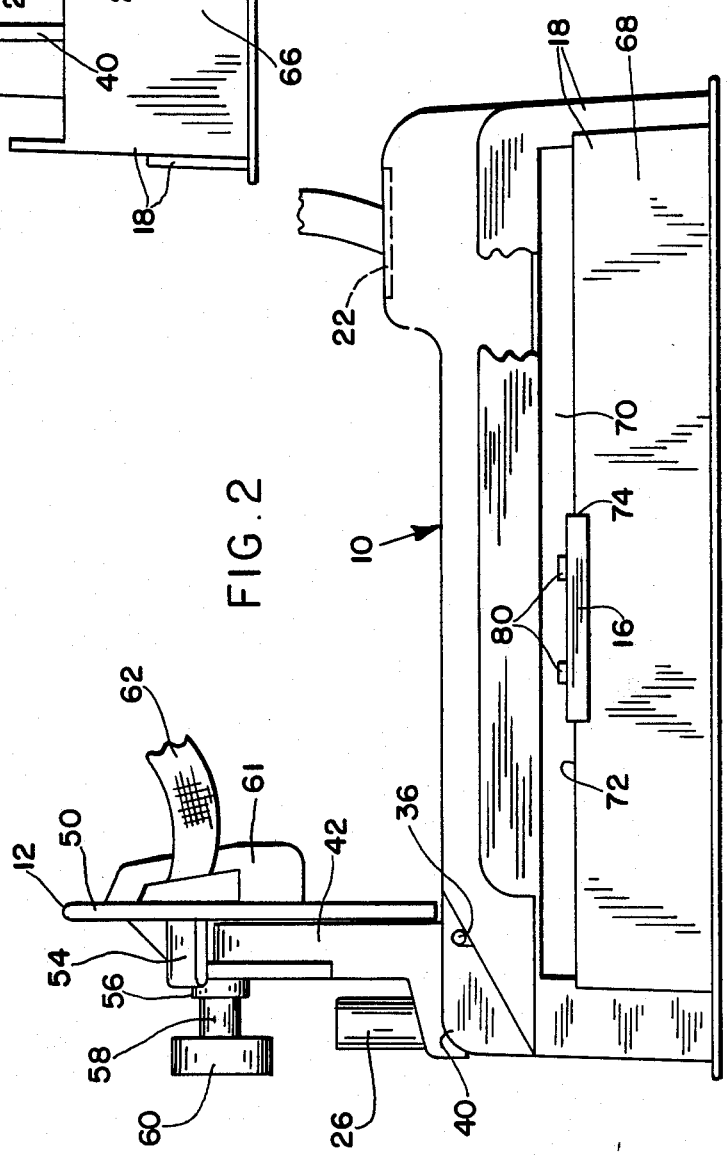

LEG AND ANKLE HOLDER FOR ASSISTING MEDICAL AND RADIOLOGICAL PROFESSIONALS IN X-RAY EXAMINATION AND FILMING OF THE ANKLE AND FOOT STRUCTURE

Continuation-in-part of Ser. No. 877,127, filed June 23, 1986, now abandoned.

FIELD OF THE INVENTION

A leg and ankle holder for assisting medical and radiological professionals in X-ray examination and filming of the ankle and foot structure.

BACKGROUND OF THE INVENTION

When there has been injury to the ankle, an orthopedist is cognizant of bone fracture, or sprains or ligament tears, and is greatly assisted by X-ray examination and filming. The foot and ankle are somewhat difficult to assess in this manner as the foot is difficult to immobilize, especially when very painful. If not properly positioned, the result is to have to repeat the X-ray which causes delay, added expense, and unnecessary addition of pain and radiation to the patient.

The medical personnel cannot rely on a patient in pain to hold his foot in a certain position to obtain the X-ray. When an orthopedic surgeon has to check the alignment of an ankle he is operating on, an unconscious person cannot hold his foot in position. It then becomes necessary for the medical personnel to actually hold the foot in the proper position. Some medical teams tie something around the foot pulling it inward as they stand at a distance away from the radiation. This results in repeating the X-ray if the positioning is incorrect.

SUMMARY OF THE INVENTION

The apparatus comprises a molded plastic leg, ankle and foot support with means to receive and hold X-ray cassettes, thus including two parallel spaced slots holding the cassettes upright for right or left lateral views. The slots are provided with stop means for the cassettes for one-half views, whereby a single film can be used for two different views. These stop means can be by-passed if it is desired to use a whole film for a single view. Where necessary, the materials used in the present apparatus are X-ray transmissive.

A foot plate is pivotally mounted on a foot plate support for adjustment about an axis relatively parallel to the body of the patient for required internal or external rotation. The foot plate support is itself pivotally adjustable on an axis at a right angle to the first axis for dorsiflexion. A clamp or lock holds the foot plate immovable in its adjusted rotation position, and the degree of dorsiflexion is held by a special screw type actuator that does not need an extraneous lock or clamp.

The foot is precisely strapped to the foot-plate and means is provided for adjustably securing the foot-plate in general upright position, or at a general right angle to, the foot support. The adjustments are dorsiflexion and internal (or external) rotation, but the foot is not twisted. These motions provide most of the positions ever needed for viewing a foot and ankle.

New and improved strap holders are provided on the foot plate. The members to be inspected must be held precisely to meet medical requirements.

The most common views of foot and ankle trauma are easily accomplished by internal or external rotation and/or dorsiflexion positions, and the present invention provides for such positioning with the least trouble and effort and the simplest structure.

BRIEF DESCRIPTION OF THE DRAWINGS

FIG. 2 is a side view of the device on a smaller scale;

FIG. 3 is an end view thereof looking at the left-hand end of the device shown in FIG. 2;

FIG. 6 is a section on line 6—6 of FIG. 3.

PREFERRED EMBODIMENT OF THE INVENTION

Figure 1:
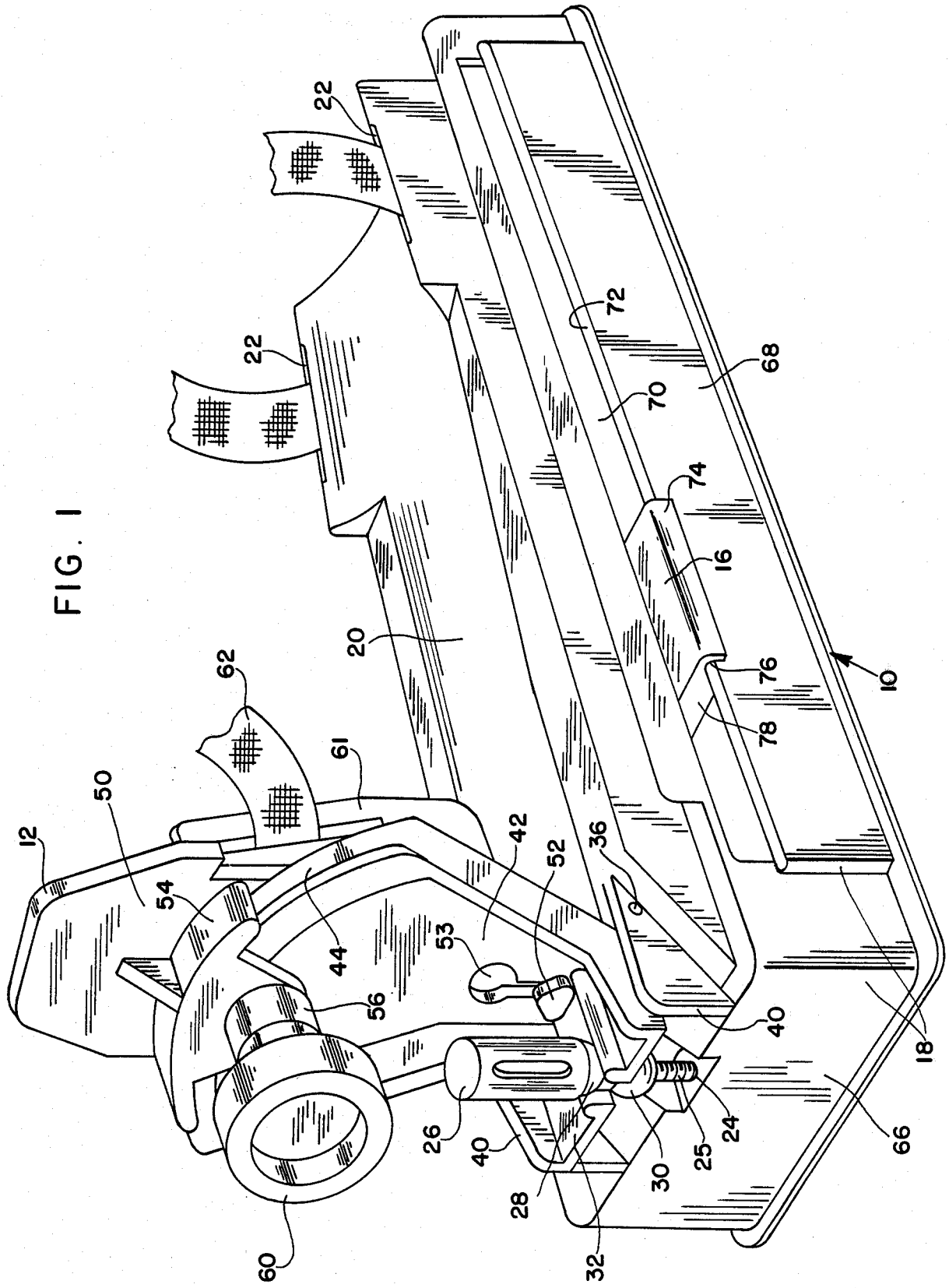
FIG. 1 is a perspective view of the present invention.

This invention is a support, positioning, and holding device for the foot, ankle and a portion of the lower leg, so that it can be X-rayed precisely. The device comprises only two main parts; a leg and heel support generally indicated at 10 and a foot holding plate 12. These parts, as well as knob 60 securing the parts together in adjusted position, and a separte X-ray cassette stop plate 16 that is selectively used, all are made of molded plastic that is capable of transmitting X-rays and can be sterilized easily. Thus the positioning device of the present invention is relatively simple but precise, easily set up and used for the intended purpose, and easily cleaned and stored.

The support 10, as seen in FIGS. 1, 2, 3, 4 and 5, has a rectangular surrounding base 18 forming a wall, and an open bottom with a cylindrically dished top 20 (FIG. 1); for the leg and heel with slotted means 22 adjacent one end to position strapping to anchor the leg. At the opposite end of leg and heel support 10 there is a vertical threaded hole 24 (FIG. 1); threadedly receiving a screw 25 that has a manual actuator handle 26 with a convex bottom 28 spaced from a ball-like member 30. Between enlargement members 28 and 30 on screw 25, there is a plate 32 that forms part of a foot plate support that is pivotally mounted at 36, 36 in a pair of parallel flanges 40 that extend up from the leg and heel support. Thus, by turning screw 25 by handle 26, the foot plate support is pivoted or rotated in part for the adjustment of dorsiflexion and the foot plate support is also held in its adjusted position.

The plate 32 of the foot plate support extends at a right angle to a generally vertical plate 42 having an arc-shaped guiding flange 44 thereon, and of course the entire foot plate support pivots about axis 36, 36. A foot plate 50 has a pin 52 that pivots in a keyhole slot 53 (FIG. 1) in the plate 42, and a flange 54 is guided by flange 44. A threaded boss 56 on the flange 54 threadedly engages a screw 58 that has a handle 60 to turn it to impinge on the rear surface of plate 42 on the foot plate support, so that the foot plate 50 may be manually pivoted or rotated to the position desired and then clamped in fixed relation to the foot plate support 42 (FIGS. 1, 3 and 6).

The foot plate 50 has a pair of spaced generally parallel ears 61 (FIGS. 1, 2 and 6) that are slotted to receive a belt 62 to secure the patient's foot to the foot plate, preferably by hook and hold means.

Figure 4:
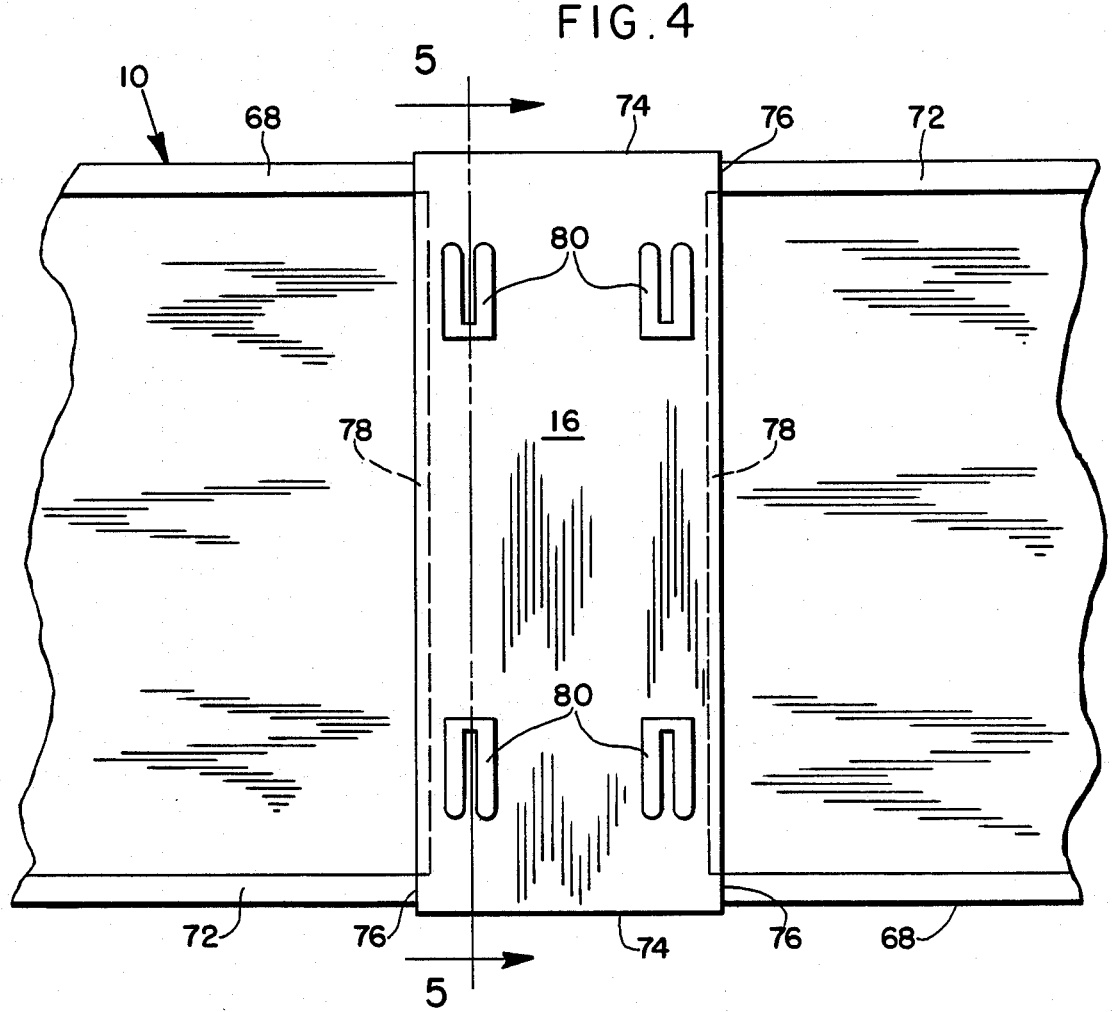
FIG. 4 is a plan view of the device shown in FIG. 1 with parts broken away.
Figure 5:
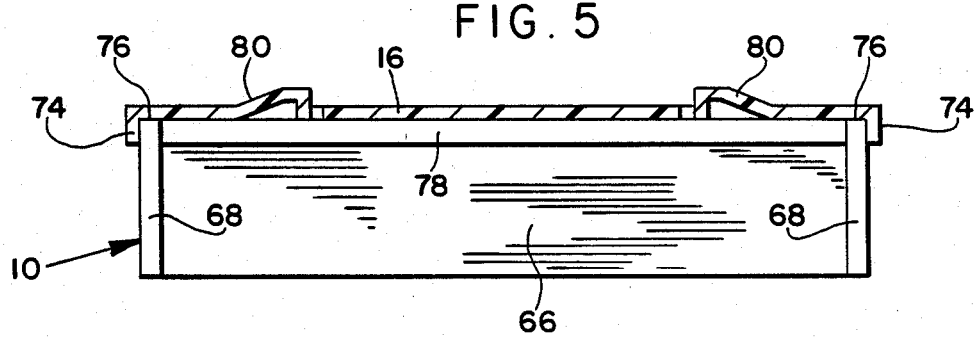
FIG. 5 is a section on line 5—5 of FIG. 4.

The support 10, having the wall 18 that positions the device, includes two short end walls 66, and two parallel long side walls 68. The latter are provided with elongated, parallel, like-sized horizontal slots 70 forming edges 72 upon which rests, or snaps onto, the cross plate 16 having downturned ends 74 that may embrace the edges 72, preferably in concomitant notches 76 in the edges, and having side edges at 78, to position plate 16. As shown in FIGS. 4 and 5, plate 16 has upwardly extending stop projections 80 near the side walls 68. The film cassette is placed on the plate 16 and edges 72, positioned by stops 80 for a one-half exposure of the film, or for a full exposure if the operator simply lifts the cassette up and over the stops and moves it to a centralized position regarding the support. Thus, if desired, a single film can be used to embody a side view and a top view of the foot, ankle, etc.

DEFINITIONS OF INTEREST

Anterior: The front of a structure.

Anterior X-ray view of the ankle: The foot is rotated 5–20 degrees internally and the toes are dorsiflexed up to 5 degrees. The X-ray cassette goes under the foot and ankle.

Posterior: Pertaining to the back of a structure.

Posterior X-ray view of the ankle: The anterior and posterior views may be taken at the same time thus positioned the same.

Lateral: Farthest from the midline or middle of the body.

Lateral X-ray view of the ankle: The foot is positioned at right angles to the leg and may be dorsiflexed up to 5 degrees. The X-ray cassette goes on the outside of the foot or the lateral side.

Oblique: A slanting direction or any variation from the perpendicular or the horizontal.

Oblique X-ray view of the ankle: The foot is externally rotated (rotated outward) up to 45 degrees and the toes are dorsiflexed up to 5 degrees. The X-ray cassette goes underneath the foot.

Dorsiflexion: The upward bending of the hand on a wrist or a foot on an ankle. Pulling the foot towards the head.

X-ray Cassette: A metal frame that holds the X-ray film. The front of the cassette is not metal which allows the film to be exposed.

Internal Rotation: Movement of a body part toward the mideline or middle of the body.

External Rotation: The movement of a body part away from the middle of the body.

I claim:

1. Ankle, foot, and leg positioning apparatus for taking an X-ray exposure, said apparatus comprising an elongated leg and heel support.
    a foot plate and a foot plate support located at a general right angle to the length of said leg and heel support at one end thereof.
    means pivotally mounting the foot plate on the foot plate support on an axis generally parallel to the length of said leg and heel support,
    means pivoting the foot plate support to the leg and heel support adjacent an end thereof on an axis transverse to the length of the leg and heel support,
    means to lock the foot plate on the foot plate support in a rotarily adjusted position thereon, and
    means to rotarily adjust the foot plate support and foot plate on said leg and heel support.

2. The apparatus of claim 1 wherein the means pivotally mounting the foot plate support on the leg and heel support in part supports the foot plate support on the leg and heel support.

3. The apparatus of claim 1 wherein the means to rotarily adjust the foot plate support in part supports the latter on the leg and heel support.

4. The apparatus of claim 1 wherein the means pivoting the foot plate support and the means adjusting the foot plate support mount the foot plate and foot plate support on the leg and heel support.

5. The apparatus of claim 1 including a flat part on the foot plate support, and means to rotarily adjust the foot plate support on the leg and heel support comprises a rotary threaded member in mesh with threads on the leg and heel support,
    means on the threaded member engaging opposite side surface of said part of the foot plate support, wherein the threaded member raises and lowers the part and rotarily adjusts the foot plate support on its axis.

6. The apparatus of claim 1 including receptacles for a film, said receptacles being at right angles to each other and comprising means to position said film to photograph the positioned ankle in two different exposures, and means in each receptacle to position film therein at a half-way location to expose only one-half the film.

7. The apparatus of claim 1 including slotted ears in spaced relation on the foot plate, said ears extending generally at right angles to the foot plate, and a foot holding strap in said slots.

8. The apparatus in claim 7 wherein the ears face the main body portion of the leg and heel support, and film holding means on the leg and heel support in cooperative position relative to the ears for exposing the film and picturing a foot held by the strap.

9. Positioning apparatus comprising an elongated leg and heel support, a foot plate support, a foot plate thereon, means pivotally mounting the foot plate support on the leg and heel support adjacent an end of the latter, said means having a pivot axis at a right angle to the length of the leg and heel support, means to cause the foot plate support to pivot on said axis to adjust the foot plate and foot plate support for dorsiflexion of a foot on the foot plate,
    means pivotally mounting the foot plate on the foot plate support on an axis generally parallel to the length of the leg and heel support, interengaging guide means on the foot plate and foot plate support guiding the plate in its pivotal motion relative to the foot plate support, to provide internal and external rotation of a foot secured on the foot plate, and
    cooperating means on the foot plate and foot plate support to clamp the foot plate to the foot plate support in adjusted position of the foot plate relative to the foot plate support.

10. The apparatus of claim 9 wherein the means to cause the foot plate support to pivot includes means maintaining the adjusted position of the foot plate support.

11. The apparatus of claim 9 wherein the means maintaining the adjusted position of the foot plate support and the means to pivot the the foot plate support on the leg and heel support comprise a screw threadedly engaged with the leg and heel support and passing through the foot plate support, and enlargements on the screw in mutually spaced relation and including between them portions of the foot plate support, said enlargements being in cooperative contact with said foot plate support portions.

* * * * *